United States Patent [19]

Howell

[11] 4,436,936

[45] Mar. 13, 1984

[54] ALKYLATION AND ARALKYLATION OF AROMATIC AMINES

[75] Inventor: Frederick H. Howell, Atherton, England

[73] Assignee: Ciba-Geigy Corporation, Ardsley, N.Y.

[21] Appl. No.: 387,082

[22] Filed: Jun. 10, 1982

[30] Foreign Application Priority Data

Jun. 19, 1981 [GB] United Kingdom ............... 8119010

[51] Int. Cl.³ ............................................. C07C 85/24
[52] U.S. Cl. .................... 564/409; 564/307; 564/308
[58] Field of Search ................... 564/409, 307, 308

[56] References Cited

U.S. PATENT DOCUMENTS

2,285,243 6/1942 Weinmayr ..................... 260/575
2,762,845 9/1956 Stroh et al. ...................... 260/578
2,814,646 11/1957 Koikn et al. ..................... 260/577

FOREIGN PATENT DOCUMENTS

468226 6/1937 United Kingdom .

OTHER PUBLICATIONS

Olah, Friedel-Crafts and Related Reactions, vol. 2, Interscience Publishers, N.Y., pp. 576-577 (1964.
Hickenbottom, J. Chem. Soc., pp. 404-407 (1937).

*Primary Examiner*—Charles F. Warren
*Assistant Examiner*—Margaret B. Medley
*Attorney, Agent, or Firm*—Michael W. Glynn

[57] ABSTRACT

Compounds having the formula I

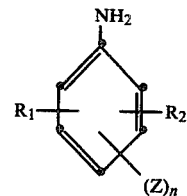

as well as salts or metal salt complexes thereof, in which formula I n, $R_1$, $R_2$ and Z have the meanings given in claim 1, can be prepared under mild reaction conditions by reacting 1.0 mole of an aromtic amine having the formula II

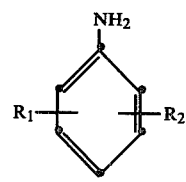

with up to three moles of an alkylating agent (III) capable of introducing a residue Z into the benzene ring of an amine (II) at a position ortho or para to the $NH_2$ group, the reaction being effected at elevated temperatures in the presence of an acid catalyst in an aqueous acid medium, containing at least 30% by weight of water, based on the acid, and optionally converting compounds (I) into salts or metal salt complexes. The compounds (I) so produced are useful in the production of intermediates for dyestuffs, additives for plastics, rubbers, oils, etc., and in the production of biologically active compounds.

13 Claims, No Drawings

ALKYLATION AND ARALKYLATION OF AROMATIC AMINES

The present invention relates to the alkylation and aralkylation of aromatic amines and to the aromatic amines when so produced.

It is known that aniline can be alkylated at temperatures generally in excess of 200° C., or at lower temperatures, provided that particularly reactive olefins are used, and water is strictly removed as it is formed.

It is an object of the present invention to provide a new method of producing an ortho- or para-alkylated aniline which is not reliant either on the use of high temperatures or specific reactive olefins, but which can employ a wide variety of alkylating agents under milder conditions than those previously used.

Surprisingly, we have now found that this objective is fully met, and the limitations of the known processes avoided, by reacting an aromatic amine with an alkylating agent in the presence of an acid catalyst and in an aqueous acid medium.

According to the present invention there is provided a process for producing a compound having the formula I

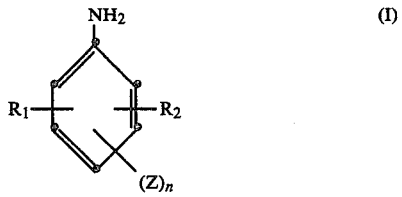

as well as salts or metal salt complexes thereof with organic or inorganic acids, in which formula I n is 1, 2 or 3, $R_1$ is H, halogen, $CF_3$, $CCl_3$, $C_1$–$C_5$ straight or branch chain alkyl or phenyl; $R_2$ is H, halogen, or $C_1$–$C_5$ straight or branch chain alkyl, and Z is linked at a position ortho or para to the $NH_2$ group and is a residue of formula

where $R_3$ is H or $C_1$–$C_4$ straight chain alkyl, $R_4$ is $C_1$–$C_4$ straight chain alkyl or phenyl and $R_5$ is $C_1$–$C_8$ straight or branch chain alkyl or phenyl or $R_3$ and $R_4$ and/or $R_4$ and $R_5$, together with the carbon atom to which they are bonded, may be a cyclohexylene ring, which process comprises reacting 1.0 mole of an aromatic amine having the formula II

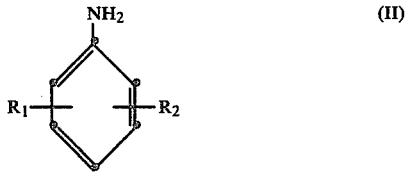

wherein $R_1$ and $R_2$ have their previous significance, with up to three moles of an alkylating agent (III) capable of introducing a residue Z into the benzene ring of amine II at a position ortho or para to the $NH_2$ group, the reaction being effected at elevated temperature in the presence of an acid catalyst in an aqueous acid medium containing at least 30% by weight of water, based on the acid used, and optionally converting the compound of formula I into a salt, or metal salt complex, with an organic or inorganic salt.

The molar proportions of amine II to alkylating agent III may vary within the range of from 10:1 to 1:3 respectively. When an excess of amine II is used, this excess may be recovered, e.g. by distillation, and recycled.

When the groups $R_1$ and $R_2$ are halogen, they may be F, Cl, Br, I, preferably F or Cl; and when the groups $R_1$ and $R_2$ are $C_1$–$C_5$ alkyl residues they may be for example a methyl, ethyl, n-propyl, isopropyl, n-butyl, sec-butyl, isobutyl, t-butyl, n-pentyl or neopentyl group. Preferred alkyl groups $R_1$ and $R_2$ are methyl and ethyl.

When the groups $R_3$ and $R_4$ are $C_1$–$C_4$ alkyl residues they may be for example a methyl, ethyl, n-propyl or n-butyl group.

When the group $R_5$ is a $C_1$–$C_8$ straight or branch chain alkyl group it may be, for example, a methyl, ethyl, n-propyl, iso-propyl, n-butyl, sec-butyl, isobutyl, n-pentyl, neopentyl, n-hexyl, n-heptyl or n-octyl group. When the residues $R_3$ and $R_4$, or $R_4$ and $R_5$, together with the carbon atom to which they are joined, form a cyclohexylene residue, the residue Z may be, for example, a 1-methyl-cyclohex-1-yl, 1-ethyl-cyclohex-1-yl, or 1-phenyl-cyclohexyl-1-yl residue.

When the residues $R_3$ and $R_4$, together with the carbon atom to which they are joined form a cyclohexylene residue and the residue $R_5$, together with the carbon atom to which it is bonded is connected to this cyclohexylene residue to form another cyclohexylene residue, the residue Z may be an adamant-1-yl residue.

Preferred products of formula I, as produced by the process of the present invention, are those wherein n and $R_1$ have their previous significance, $R_2$ is H and $R_3$ is H or $CH_3$, $R_4$ is $CH_3$ and $R_5$ is $C_1$–$C_8$ alkyl or phenyl. More preferred are those products, as produced by the process of the present invention, wherein n has its previous significance, $R_1$ is H or halogen, preferably Cl, $R_2$ is H, $R_3$ is H or $CH_3$, $R_4$ is $CH_3$ and $R_5$ is $C_1$–$C_8$ alkyl or phenyl.

Suitable salts of compounds of formula I are, e.g., hydrochlorides, hydrobromides, sulphates, phosphates, methane sulphonates, p-toluene sulphonates, formates, oxalates, adipates and isophthalates. Examples of metal salt complexes are the zinc chloride and stannous chloride complexes.

Examples of compounds of formula I produced by the process of the invention include: 4-t-butyl-aniline, 4-(1,1,3,3-tetramethyl-butyl)-aniline, 4-(adamant-1-yl)-aniline, 4-cumyl-aniline, 2-cumyl-aniline, 2-isopropyl-aniline, 4-isopropyl-aniline, 2,4di-isopropyl-aniline, 2,6-di-isopropyl-aniline, 2,4,6-tri-isopropyl-aniline, 4-cyclohexyl-aniline, 4-(1-methyl-cyclohex-1-yl)-aniline, 4-t-butyl-2-methyl-aniline, 4-cumyl-2-methyl-aniline, 2-cumyl-5-methyl-aniline, 2-cumyl-4-methyl-aniline, 4-cumyl-2,6-dimethyl-aniline, 4-cumyl-2-ethyl-aniline, 4-cumyl-2,6-diethyl-aniline, 4-cumyl-2-isopropyl-aniline, 4-cumyl-2,6-diisopropyl-aniline, 4-cumyl-2-sec.butyl-aniline, 4-cumyl-2-ethyl-6-methyl-aniline, 4-cumyl-2-isopropyl-6-methyl-aniline, 4-cumyl-2-sec.butyl-6-methyl-aniline, 4-cumyl-2-sec.butyl-6-ethyl-aniline, 4-cumyl-2-phenyl-aniline, 2-chloro-4-t-butyl-aniline, 4-(adamant-1-yl)-2-chloro-aniline, 2-chloro-4-cumyl-aniline, 2-chloro-4-cumyl-5-methyl-aniline, 4-t-butyl-2,6- dichloro-aniline, 4-(adamant-1-yl)-2,6-dichloro-aniline, 4-cumyl-2,6-dichloro-aniline, 4-cumyl-2,3-dichloro-aniline, 4-cumyl-2,5-dichloro-aniline, 2-bromo-4-cumyl-aniline, 4-cumyl-2-fluoro-aniline, 4-cumyl-3-fluoro-aniline, 4-cumyl-2-trifluoromethyl-aniline, and 4-cumyl-2-trichloromethyl-aniline.

The reaction between the aromatic amine of formula II and the alkylating agent III is preferably effected in the presence of a metal salt, as co-catalyst, and optionally at superatmospheric pressure.

Alkylating agents III which are reacted with amine II contain a reactive centre e.g. an olefinic, hydroxy, amino, halogen or ether group, which is eliminated, transformed or rearranged during the course of the alkylation reaction. It is presumed that the reaction proceeds via a carbonium ion mechanism, therefore the order of preference of alkylating agents is those providing tertiary, preferred to those providing secondary, preferred to those providing primary carbonium ions.

It is an essential feature of the process of the invention that at least 30% by weight, based on the acid used, of water is present in the reaction mixture. The presence of this substantial amount of water, relative to acid, is important in order to ensure that the reaction mixture forms a homogeneous solution. In preferred instances in which the acid used is hydrochloric acid, the amount of water which is preferably used is 64% by weight relative to HCl viz. the commercially available concentrated HCl (36% weight/weight). Clearly, relative to the total reaction mixture, large excesses of water are to be avoided in the interest of output efficiency from a given reactor volume.

If desired, a further solvent may be present provided that it remains inert during the reaction.

The reaction is effected at an elevated temperature, e.g. a temperature in the range of from 30° to 250° C., more preferably in the range of from 100° to 190° C. When reaction temperatures of above 110° C. are used, then superatmospheric pressures may be applied in a suitable pressure vessel e.g. a sealed glass reactor or an acid-resistant pressure vessel e.g. a tantalum lined reactor. Any superatmospheric pressure used is preferably below 100 atmospheres.

A further essential feature of the process of the invention is the use of an acid as catalyst. The acid may be inorganic or organic or a partial salt thereof. Examples of such acids are hydrochloric, sulphuric and orthophosphoric acids; alkyl-, aryl- or aralkyl-substituted inorganic acids e.g. methane- or ethane- sulphonic acids, benzene sulphonic acid, p-toluene sulphonic acid and methane phosphonic acid; dichloro-acetic acid, trichloroacetic acid or trifluoroacetic acid. The proportion of acid catalyst present relative to 1.0 mole of aromatic amine is preferably in the range 0.25 to 1.5 moles and especially 0.5 to 1.0 mole. The preferred acid is hydrochloric acid. The alkylation is preferably carried out in the presence of a co-catalyst which is a metal salt, oxide, hydroxide or carbonate and where the metal belongs to group II, III or VIII of the Periodic Table of Elements. Such metals are preferably Mg, Cd, Zn, Al, Fe, Co and Ni. The metal salt is preferably that which shares the ion common to the acid used to catalyse the reaction and may be halide, sulphate or phosphate, for example. If a metal carbonate, oxide or hydroxide is employed as co-catalyst, then sufficient of the acid over and above that required to catalyse the alkylation should be present so as to form the metal salt. The metal salt may be present in a concentration of up to 1.0 mole, especially within the range 0.25 to 0.5 mole per mole of aromatic amine. The preferred metal halide for use as cocatalyst is $ZnCl_2$.

After completion of the alkylation, the alkylated aromatic amine is freed from the acid or acid/metal salt complex by treatment with a base. Suitable bases for this purpose are alkali metal hydroxides, carbonates, bicarbonate, and ammonium hydroxide. The preferred bases are sodium and ammonium hydroxide. These bases are especially preferred in the instance where the co-catalyst is $ZnCl_2$ where the initially precipitated basic zinc salts are readily dissolved up again with the excess base and enable the alkylated aromatic amine to be readily isolated.

Examples of amines of formula II are: aniline, o,m and p-toluidine, o-ethylaniline, o-isopropylaniline, o-sec-butylaniline, o- and m-fluoroaniline, o-chloroaniline, o-bromoaniline, 2,6-dimethylaniline, 2,6-diethylaniline, 2,6-diisopropylaniline, 2-ethyl-6-methylaniline, 2-methyl-6-isopropylaniline, 2-sec.-butyl-6-methylaniline, 2-sec.butyl-6-ethylaniline, 2-chloro-5-methylaniline, 2-chloro-6-methylaniline, 5-chloro-2-methylaniline, 2-phenylaniline, 2,6-dichloroaniline, 2,3-dichloroaniline, 2,5-dichloroaniline, 2-trifluoromethylaniline, and 2-trichloromethylaniline.

The alkylating agent III used in the process of the present invention may be an olefin, alcohol, alkylamine, alkyl halide or ether which is capable of introducing a residue Z into the benzene nucleus of the aromatic amine of formula II. The reactive centre contained in the alkylating agent III may be hydrogen, OH, halogen, an olefinic bond or an $NH_2$ group on a tertiary carbon atom. Examples of alkylating agents III are:

(a) Olefins

The olefin may be straight or branched chain, cyclic, or substituted by phenyl. Examples of olefins suitable for (ar)alkylation of aromatic amines are: propylene, butene-1, butene-2 (cis or trans), pentene-1, pentene-2 (cis or trans), hexene-1, hexene-2 (cis or trans), heptene-1, octene-1, isobutylene, 2-methylbutene-1, 2-methylpentene-1, 2,4-dimethylpentene-1, 2,5-dimethylhexene-1, 2,4,4-trimethylpentene-1 and 2,4,4-trimethylpentene-2 (diisobutylene), cyclohexene, 1-methylcyclohex-1-ene, 1-ethylcyclohex-1-ene, 1-phenylcyclohex-1-ene, styrene, α-methylstyrene.

(b) Alcohols

Alcohols may be used as the alkylating agent. The alcohol may be linear, branched, cyclic or phenyl-substituted alkyl. Primary, secondary or tertiary alcohols may be used. In particular tertiary alcohols are preferred to secondary, which in turn are preferred to primary. It will be appreciated however that certain primary alcohols under the conditions of the process may rearrange to give a more preferred secondary or tertiary carbonium ion. Suitable examples of such alcohols for alkylation of aromatic amines include: isopropanol, n-butanol, iso-butanol, sec-butanol, tert-butanol, 2-methylbutan-2-ol, 1-methylcyclohexan-1-ol, 1-methylcyclohexan-2-ol, 1-isopropylcyclohexan-2-ol, α,α-dimethylbenzyl alcohol, 2,5-dimethylhexan-2-ol, 2,4-dimethylpentan-2-ol, and 1-adamantanol.

(c) Amines

Tertiary alkyl substituted amines containing an amino group on a tertiary carbon atom may be used to alkylate aromatic amines, e.g. tert-butylamine.

(d) Halides

Alkyl halides may be primary, secondary or tertiary. The halide may have a linear or branched chain, and it may be an alkyl, cycloalkyl or phenylalkyl halide. Examples of such compounds include: tertbutylchloride, 2,4,4-trimethyl-2-chloropentane or α,α-dimethylbenzylchloride.

(e) Ethers

Ethers may be dialkyl or alkylphenyl. Examples of such compounds are: α,α-dimethylbenzylmethyl ether and phenyl tert-butyl ether.

Of the above alkylating agents, olefins and alcohols are to be preferred. In general, alkylating agents which provide a tertiary carbonium ion are preferred. Alkylating agents that are particularly preferred include: isobutylene, diisobutylene, propylene and α-methylstyrene.

The process of the present invention may be applied to the (ar)alkylation or a wide range of alkyl-, phenyl-, haloalkyl-, and halonuclear substituted aromatic amines, ranging from aniline itself to multi-substituted anilines, which substituents may be found at the carbon atoms of the benzene ring.

In contrast, the processes of the prior art can be applied only to aniline or simple derivatives thereof e.g. p-aminophenol, o- or p-anisidine or esters of anthranilic acid.

The process of the present invention can utilise a wide range of alkylating agents having a broad spectrum of molecular weight i.e. from $C_3$ to $C_{16}$, including olefins, alcohols, amines, halides and ethers. In the process of the invention, milder conditions of temperature and pressure are applied relative to those used in known processes.

Compounds of formula I are useful in the production of intermediates for dyestuffs, additives for plastics (see e.g. British Patent Specification No. 1,347,008), rubbers, oils etc. and in the production of biologically active compounds (see e.g. British Patent Specification Nos. 1,219,698 and 1,250,224).

The following Examples further illustrate the present invention. Parts and percentages are by weight unless otherwise stated. All pressures shown therein are expressed in millibars.

EXAMPLE 1

279 parts of aniline, 222 parts of tertiary butyl alcohol and 153 parts of 36% w/w aqueous hydrochloric acid, in which had previously been dissolved 102 parts of anhydrous zinc chloride, are sealed into a liter tantalum lined autoclave and stirred at 175° C. for 90 hours. The cooled reaction mixture, after discharging from the autoclave, is treated with 750 parts of sodium hydroxide in 1500 parts of water. The organic phase is separated off, washed with water, and distilled to give 407 parts of a fraction $mb_{20}70°-150°$ C.GLC [gas liquid chromatography] analysis of the distillate shows it to contain the following components: Aniline 7.2% by weight, p-tert-butylaniline 82.0% by weight [Literature b.p. is 228°-230° C., m.p. 17° C.], 2,4-ditert-butylaniline 4.6% by weight. The yield of p-t-butylaniline is 75%.

EXAMPLE 2

The procedure described in Example 1 is repeated using 336 parts of diisobutylene in place of the tert-butyl alcohol. Distillation gives 411 parts of a fraction $mb_{20}60°-180°$ C. which GLC analysis shows to have the following percentage composition by weight: Aniline 21.9% by weight, p-tert-butylaniline 2.5% by weight, p-(1,1,3,3-tetramethylbutyl)aniline 71.4% by weight, Unknowns 4.2% by weight. The yield of p-(1,1,3,3-tetramethyl-butyl)aniline is 48%. Fractional distillation of the above fraction gives pure p-(1,3,3,3-tetramethyl-butyl)-aniline $mb_{20}153°-4°$ C. [Literature $mb_7$ 112°–115° C.] having the following percentage composition by weight:

|  | Carbon | Hydrogen | Nitrogen |
|---|---|---|---|
| Found | 81.89 | 11.29 | 6.96 |
| Calculated for $C_{14}H_{23}N$ | 81.89 | 11.29 | 6.82. |

EXAMPLE 3

14.0 parts of aniline, 15.3 parts of 36% w/w hydrochloric acid, 10.2 parts of zinc chloride and 11.4 parts of 1-adamantanol are sealed into a glass tube and placed in a rocking autoclave pressurised to 20 atmospheres with nitrogen. After rocking at 175° C. for 33 hours, the reaction product, after decomposition with 50 parts of sodium hydroxide in 100 parts of water, yields 13.3 parts of 4-(1-adamantyl)aniline $mb_{0.7}$ 174°–6° C. (78% yield). Crystallisation from ethanol gives colourless plates m.p. 106°-8° C. (literature 105° C.) with the following percentage composition by weight:

|  | Carbon | Hydrogen | Nitrogen |
|---|---|---|---|
| Found | 84.30 | 9.07 | 6.08 |
| Calculated for $C_{16}H_{21}N$ | 84.53 | 9.31 | 6.16. |

EXAMPLE 4

18.6 Parts of aniline, 20.4 parts of 36% w/w hydrochloric acid containing 13.6 parts of zinc chloride are stirred and refluxed for 24 hours with 23.6 parts of α-methylstyrene. The work-up follows Example 3 and gives on distillation 32.9 parts of 4-cumylaniline $mb_4$ 175°–80° C. (78% yield based on a 93% purity by G.L.C.).

Purification is achieved by hydrolysis of the N-acetyl derivative m.p. 129°-31° C., and pure 4-cumylaniline has $mb_4$ 166°-8° C. and the following percentage composition by weight:

|  | Carbon | Hydrogen | Nitrogen |
|---|---|---|---|
| Found | 85.23 | 8.19 | 6.66 |
| Calculated for $C_{15}H_{17}N$ | 85.26 | 8.11 | 6.63. |

EXAMPLE 5

18.6 Parts of aniline, 38.0 parts of p-toluene sulphonic acid monohydrate, 25 parts of water, and 23.6 parts of α-methylstyrene are stirred and refluxed for 24 hours. The organic phase still present at the end of this period is removed after dilution with ether and the aqueous phase then made alkaline with sodium hydroxide solution. The organic phase is then isolated with ether to give 14.6 parts $mb_{20}$ 186°-214° C. G.L.C. analysis of the distillate shows it to contain the following components: 2-cumylaniline 15.1% by weight, α-methylstyrene dimer 21.5% by weight, 4-cumylaniline 60.2% by weight.

EXAMPLE 6

9.3 Parts of aniline, 10.2 parts of 36% w/w hydrochloric acid, 6.8 parts of zinc chloride and 12.6 parts of propylene are sealed into a glass tube and placed in a rocking autoclave pressurised to 60 atmospheres with nitrogen. After rocking at 175° C. for 60 hours the reaction product is treated with 25 parts sodium hydroxide in 50 parts of water and yields on distillation 19.5 parts of a fraction $mb_{20}$ 120°–155° C. Analysis of the distillate by GLC shows it to contain the following components: Aniline 0.9% by weight, o-isopropylaniline 2.3% by weight, p-isopropylaniline 2.3% by weight, 2,6-diisopropylaniline 5.0% by weight, 2,4-diisopropylaniline 7.5% by weight, 2,4,6-triisopropylaniline 64.1% by weight.

The general methods described for the previous Examples are also used for the preparation of Examples 7 to 27 summarised in Table 1.

TABLE I

| Ex. No. | Starting materials/ reaction conditions | Product | b.p. °C. pressure (mb) | m.p. °C. | Molecular Formula | Found and required % composition C | H | N |
|---|---|---|---|---|---|---|---|---|
| 7 | 21.4 parts o-toluidine/23.6 parts α-methylstyrene, 17 hours at reflux | 4-cumyl-2-methyl-aniline | 207–10 20 mb | 54–5 | $C_{16}H_{19}N$ | 85.27 85.28 | 8.54 8.50 | 6.03 6.22 |
| 8 | 21.4 parts m-toluidine/23.6 parts α-methylstyrene, 17 hours at reflux | 2-cumyl-5-methyl-aniline | 209–54 20 mb | HCL salt 100–10 decomp. | $C_{16}H_{20}ClN$ | 73.42 73.40 | 7.79 7.70 | 5.07 5.35 |
|  |  | 4-cumyl-3-methyl-aniline |  | 71–3 | $C_{16}H_{19}N$ | 85.59 85.28 | 8.25 8.50 | 5.96 6.22 |
|  |  | 4,6-di-cumyl-3-methyl-aniline |  | 184–6 | $C_{25}H_{29}N$ | 87.55 87.41 | 8.80 8.51 | 3.90 4.08 |
| 9 | 21.4 parts p-toluidine/23.6 parts α-methylstyrene, 17 hours at reflux | 2-cumyl-4-methyl-aniline | 192–7 20 mb | 69–71 | $C_{16}H_{19}N$ | 84.49 85.28 | 8.45 8.50 | 6.48 6.22 |
| 10 | 24.2 parts 2,6-dimethylaniline/ 23.6 parts α-methylstyrene, 6 hours at reflux | 4-cumyl-2,6-di-methyl-aniline | 142–7 0.3 mb |  | $C_{17}H_{21}N$ | 85.59 85.30 | 8.82 8.85 | 5.70 5.85 |
| 11 | 18.6 parts aniline/18.4 parts benzhydrol 3 hours at reflux | 2-(diphenylmethyl)-aniline | 178–186 0.3 mb | 126 | $C_{19}H_{17}N$ | 87.68 87.99 | 6.62 6.61 | 4.94 5.40 |
|  |  | 4-(diphenylmethyl)-aniline |  | 85–7 | $C_{19}H_{17}N$ | 87.98 87.99 | 6.75 6.61 | 5.32 5.40 |
|  |  | 2,4-di-(diphenylmethyl)-aniline |  | 118–120 | $C_{32}H_{27}N$ | 90.17 90.31 | 6.33 6.40 | 2.91 3.29 |
| 12 | 29.8 parts 2,6-diethylaniline/ 23.6 parts α-methylstyrene, 20 hours at reflux | 4-cumyl-2,6-di-ethyl-aniline | 172–84 0.9 mb | 36–7 | $C_{16}H_{25}N$ | 85.74 85.34 | 9.16 9.42 | 5.15 5.24 |
| 13 | 33.8 parts 2-phenylaniline/ 23.6 parts α-methylstyrene, 3 hours at reflux | 4-cumyl-2-phenyl-aniline | 195 0.7 mb |  | $C_{21}H_{21}N$ | 87.50 87.80 | 7.49 7.32 | 4.52 4.88 |
| 14 | 25.5 parts o-chloroaniline/ 11.2 parts isobutylene, 150° C., 36 hours sealed tube | 2-chloro-4-tert. butyl-aniline | 125–8 20 mb |  | $C_{10}H_{15}ClN$ | 65.33 65.38 | 7.64 7.68 | 7.87 7.63 |
| 15 | 25.5 parts o-chloroaniline/ 15.2 parts 1-adamantanol, 150° C., 33 hours sealed tube | 4-(1-adamantyl)-2-chloroaniline | 174–7 0.5 mb | 132–3 | $C_{16}H_{20}ClN$ | 73.18 73.40 | 7.69 7.70 | 5.21 5.35 |
| 16 | 25.5 parts o-chloroaniline/ 23.6 parts α-methylstyrene, 17 hours at reflux | 2-chloro-4-cumyl-aniline | 156 0.4 mb |  | $C_{15}H_{16}ClN$ | 73.84 73.31 | 6.77 6.56 | 5.75 5.70 |
| 17 | 28.3 parts 2-chloro-6-methyl-aniline/23.6 parts 2-methylstyrene, 20 hours at reflux | 2-chloro-4-cumyl-6-methylaniline | 146 0.3 mb | 61–2 | $C_{16}H_{19}ClN$ | 74.12 73.97 | 7.04 6.99 | 5.23 5.39 |
| 18 | 28.3 parts 2-chloro-5-methyl-aniline/23.6 parts α-methylstyrene, 18 hours at reflux | 2-chloro-4-cumyl-5-methylaniline | 222 20 mb |  | $C_{16}H_{18}ClN$ | 74.03 73.97 | 7.07 6.98 | 5.17 5.39 |
| 19 | 32.4 parts 2,6-dichloroaniline/ 22.4 parts diisobutylene, 125° C., 60 hours sealed tube[1] | 4-tert-butyl-2,6-di-chloroaniline | 144 20 mb |  | $C_{10}H_{13}Cl_2N$ | 55.01 55.06 | 5.98 6.01 | 6.70 6.42 |
| 20 | 16.2 parts 2,6-dichloroaniline/ 7.8 parts 1-adamantanol, 150° C., 33 hours sealed tube[2] | 4-(1-adamantyl)-2,6-dichloroaniline | 188–90 0.5 mb | 132–3 | $C_{16}H_{19}Cl_2N$ | 65.24 64.87 | 6.72 6.46 | 4.63 4.73 |
| 21 | 32.4 parts 2,6-dichloroaniline/ 23.6 parts α-methylstyrene, 24 hours at reflux | 4-cumyl-2,6-dichloro-aniline |  | 92–2 | $C_{15}H_{15}Cl_2N$ | 64.54 64.29 | 5.64 5.40 | 5.26 5.00 |
| 22 | 32.4 parts 2,3-dichloroaniline/ 23.6 parts α-methylstyrene, 48 hours at reflux | 4-cumyl-2,3-dichloro-aniline | 140–80 0.4 mb | N—acetyl-134–6 | $C_{17}H_{17}Cl_2NO$ | 63.20 63.36 | 5.18 5.32 | 4.55 4.35 |
| 23 | 32.4 parts 2,5-dichloroaniline/ 23.6 parts α-methylstyrene, 24 hours at reflux | 4-cumyl-2,5-dichloro-aniline | 140–65 0.5 mb | 65–7 | $C_{15}H_{15}Cl_2N$ | 64.31 64.29 | 5.59 5.40 | 4.73 5.00 |
| 24 | 34.4 parts 2-bromoaniline/ 23.6 parts α-methylstyrene, 5 hours at reflux | 2-bromo-4-cumyl-aniline | 162–70 0.5 mb |  | $C_{15}H_{16}BrN$ | 62.05 62.08 | 5.56 5.56 | 4.60 4.83 |
| 25 | 22.2 parts o-fluoroaniline/ 23.6 parts α-methylstyrene, 11 hours at reflux | 4-cumyl-2-fluoro-aniline | 138–52 0.8 mb | 51–2 | $C_{15}H_{16}FN$ | 78.32 78.57 | 6.92 7.04 | 6.36 6.11 |
| 26 | 22.2 parts m-fluoroaniline/ 23.6 parts α-methylstyrene, 3 hours at reflux | 4-cumyl-3-fluoro-aniline | 140–59 0.8 mb | 79–81 | $C_{15}H_{16}FN$ | 78.75 78.57 | 6.97 7.04 | 5.98 6.11 |
| 27 | 32.2 parts 2-trifluoromethyl-aniline/23.6 parts α-methylstyrene, | 4-cumyl-2-trifluoro-methylaniline | 178–80 20 mb | 44–7 | $C_{16}H_{16}F_3N$ | 68.76 68.80 | 5.83 5.78 | 5.10 5.02 |

TABLE I-continued

| Ex. No. | Starting materials/ reaction conditions | Product | b.p. °C. pressure (mb) | m.p. °C. | Molecular Formula | Found and required % composition C | H | N |
|---|---|---|---|---|---|---|---|---|
| | 1 hour at reflux | | | | | | | |

[1] with the addition of 20 parts of water
[2] with the addition of 10 parts of water, 10.2 parts of 36% aq. HCl and 6.8 parts of $ZnCl_2$
All experiments carried out with the addition of 20.4 parts of 36% aq. HCl and 13.6 parts of $ZnCl_2$, unless indicated otherwise.

What we claim is:

1. A process for producing a compound having the formula I

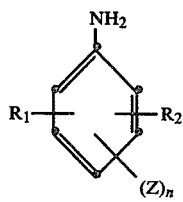

as well as salts or metal salt complexes thereof with organic or inorganic acids, in which formula I n is 1, 2 or 3, $R_1$ is H, halogen, $CF_3$, $CCl_3$, $C_1$–$C_5$ straight or branch chain alkyl or phenyl, $R_2$ is H, halogen, or $C_1$–$C_5$ straight or branch chain alkyl, and Z is linked at a position ortho or para to the $NH_2$ group and is a residue of formula

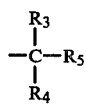

wherein $R_3$ is H or $C_1$–$C_4$ straight chain alkyl, $R_4$ is $C_1$–$C_4$ straight chain alkyl or phenyl and $R_5$ is $C_1$–$C_8$ straight or branch chain alkyl or phenyl, or $R_3$ and $R_4$ and/or $R_4$ and $R_5$, together with the carbon atom to which they are bonded, may be a cyclohexylene ring, which comprises reacting 1.0 mole of an aromatic amine having the formula II

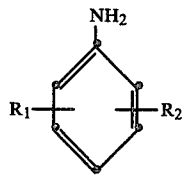

wherein $R_1$ and $R_2$ have their previous significance, with up to three moles of an alkylating agent (III) capable of introducing a residue Z into the benzene ring of an amine of formula II at a position ortho or para to the $NH_2$ group, the reaction being effected at elevated temperature in the presence of an acid catalyst in an aqueous acid medium containing at least 30% by weight of water, based on the acid used, and optionally converting the compound of formula I into a salt, or metal salt complex, with an organic or inorganic salt.

2. A process according to claim 1 wherein the molar proportion of amine II to alkylating agent III is from 10:1 to 1:3.

3. A process according to claim 1 wherein, in the compound of formula I, n and $R_1$ are as defined in claim 1, $R_2$ is H, $R_3$ is H or $CH_3$, $R_4$ is $CH_3$ and $R_5$ is $C_1$–$C_8$ alkyl or phenyl.

4. A process according to claim 1 wherein, in the compound of formula I, n is as defined in claim 1, $R_1$ is H or halogen, $R_2$ is H, $R_3$ is H or $CH_3$, $R_4$ is $CH_3$ and $R_5$ is $C_1$–$C_8$ alkyl or phenyl.

5. A process according to claim 1 wherein the reaction is effected at a temperature in the range of from 30° to 250° C.

6. A process according to claim 1 wherein the reaction is effected at a temperature in the range of from 100° to 190° C.

7. A process according to claim 1 wherein the reaction temperature is above 110° C. and a superatmospheric pressure of less than 100 atmospheres is applied.

8. A process according to claim 1 wherein the acid catalyst is hydrochloric acid.

9. A process according to claim 1 wherein the reaction is effected in the presence of a co-catalyst which is a metal salt, oxide, hydroxide or carbonate of a metal of Group II, III or VII of the Periodic Table of Elements.

10. A process according to claim 9 wherein the metal salt is present in a concentration of up to 1 mole per mole of aromatic amine.

11. A process according to claim 9 wherein the co-catalyst is $ZnCl_2$.

12. A process according to claim 1 wherein the alkylating agent III is an olefin, an alcohol, an alkylamine, an alkyl halide or ether which is capable of introducing a residue Z into the benzene nucleus of the aromatic amine of formula II.

13. A process according to claim 1 wherein the alkylating agent is isobutylene, diisobutylene, propylene or α-methylstyrene.

* * * * *